US012626798B1

(12) United States Patent
Wang et al.

(10) Patent No.: US 12,626,798 B1
(45) Date of Patent: May 12, 2026

(54) SYSTEMS AND METHODS FOR CORRELATING MEDICAL IMAGES WITH MEDICAL REPORTS

(71) Applicants: Shanghai United Imaging Intelligence Co., Ltd., Shanghai (CN); Henan Provincial People's Hospital, Zhengzhou (CN)

(72) Inventors: Meiyun Wang, Zhengzhou (CN); Dinggang Shen, Shanghai (CN); Yaping Wu, Zhengzhou (CN); Yan Bai, Zhengzhou (CN); Wei Wei, Zhengzhou (CN); Lingzhi Hu, Shanghai (CN); Tuoyu Cao, Shanghai (CN); Jianmin Yuan, Shanghai (CN)

( * ) Notice: Subject to any disclaimer, the term of this patent is extended or adjusted under 35 U.S.C. 154(b) by 0 days.

(21) Appl. No.: 19/422,097

(22) Filed: Dec. 16, 2025

(30) Foreign Application Priority Data

Dec. 3, 2025 (CN) .......................... 202511806310.7

(51) Int. Cl.
　　*G16H 15/00* (2018.01)
　　*G06N 3/0455* (2023.01)
　　　　　(Continued)

(52) U.S. Cl.
　　CPC ........... *G16H 15/00* (2018.01); *G06N 3/0455* (2023.01); *G16H 30/20* (2018.01); *G16H 30/40* (2018.01); *G06T 2207/10088* (2013.01)

(58) Field of Classification Search
　　CPC ........ G16H 15/00; G16H 30/00; G16H 30/20; G16H 30/40; G06N 3/045; G06N 3/0455; G06T 2207/10088
　　See application file for complete search history.

(56) References Cited

U.S. PATENT DOCUMENTS

2024/0354948 A1* 10/2024 Oktay .................... G06F 40/30

FOREIGN PATENT DOCUMENTS

CN 115662565 A 1/2023
CN 115830017 A 3/2023
　　　　　(Continued)

OTHER PUBLICATIONS

Bai, Q., Zou, X., Alhaskawi, A., Dong, Y., Zhou, H., Ezzi, S. H. A., . . . & Lu, H. (2025). Multi-view contrastive learning and symptom extraction insights for medical report generation. Scientific Reports, 15(1), 17991. (Year: 2025).*

(Continued)

*Primary Examiner* — Gregory A Morse
*Assistant Examiner* — Rohan Tejas Mukundhan
(74) *Attorney, Agent, or Firm* — Zhong Law, LLC

(57) ABSTRACT

Described herein are method, system, and apparatus for correlating medical images with a medical report. An apparatus may obtain a plurality of medical images of a patient and a medical report for the patient, wherein the plurality of medical images may be associated with respective sequence labels and respective view labels, and wherein the medical report may include multiple diagnoses. The apparatus may determine and fuse respective image-type embeddings and image-content embeddings for the plurality of medical images into a combined image feature representation. The apparatus may further encode the features of the medical report into a text feature representation and calculate a similarity score based on the image feature representation and the text feature representation to indicate a correlation between the medical images and the medical report.

20 Claims, 6 Drawing Sheets

(51) Int. Cl.
  G16H 30/20 (2018.01)
  G16H 30/40 (2018.01)

(56) References Cited

FOREIGN PATENT DOCUMENTS

| | | | |
|---|---|---|---|
| CN | 117809794 A | 4/2024 | |
| CN | 119444994 A | 2/2025 | |

OTHER PUBLICATIONS

Wei, Z., Jin, K., & Zhou, X. (2023). Masked contrastive reconstruction for cross-modal medical image-report retrieval. arXiv preprint arXiv:2312.15840. (Year: 2023).*

Kamal, S., & Oates, T. (2025). MedGrad E-CLIP: Enhancing Trust and Transparency in AI-Driven Skin Lesion Diagnosis. arXiv preprint arXiv:2501.06887. (Year: 2025).*

Li, L., Chen, Y. C., Cheng, Y., Gan, Z., Yu, L., & Liu, J. (Nov. 2020). Hero: Hierarchical encoder for video+ language omni-representation pre-training. In Proceedings of the 2020 conference on empirical methods in natural language processing (EMNLP) (pp. 2046-2065). (Year: 2020).*

First Office Action received for CN Application No. 202511806310.7, dated Jan. 14, 2026.

Search Report received for CN Application No. 202511806310.7, dated Jan. 13, 2026.

* cited by examiner

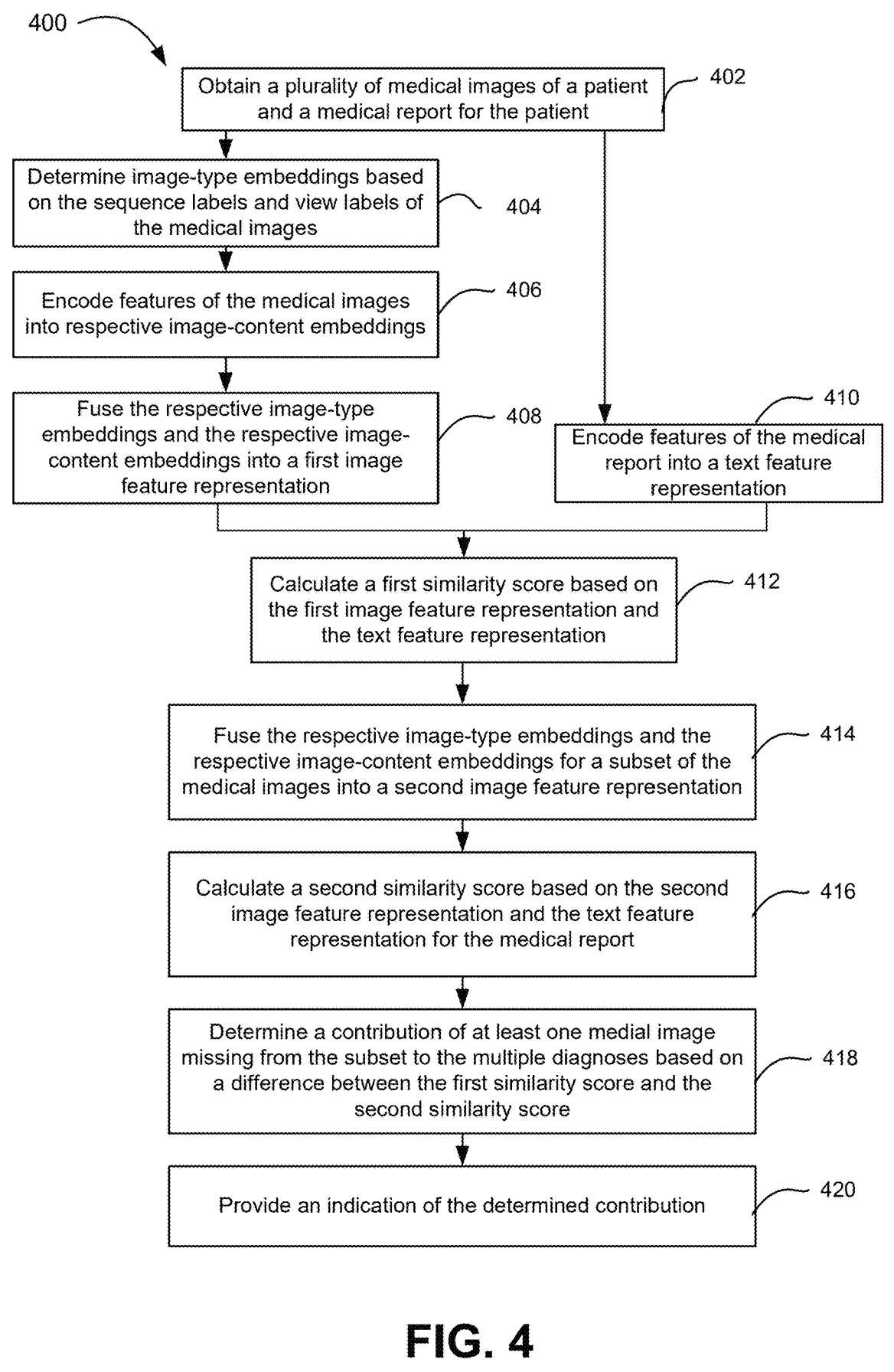

400

Obtain a plurality of medical images of a patient and a medical report for the patient — 402

Determine image-type embeddings based on the sequence labels and view labels of the medical images — 404

Encode features of the medical images into respective image-content embeddings — 406

Fuse the respective image-type embeddings and the respective image-content embeddings into a first image feature representation — 408

Encode features of the medical report into a text feature representation — 410

Calculate a first similarity score based on the first image feature representation and the text feature representation — 412

Fuse the respective image-type embeddings and the respective image-content embeddings for a subset of the medical images into a second image feature representation — 414

Calculate a second similarity score based on the second image feature representation and the text feature representation for the medical report — 416

Determine a contribution of at least one medial image missing from the subset to the multiple diagnoses based on a difference between the first similarity score and the second similarity score — 418

Provide an indication of the determined contribution — 420

FIG. 4

SYSTEMS AND METHODS FOR CORRELATING MEDICAL IMAGES WITH MEDICAL REPORTS

BACKGROUND

Radiological assessment of medical images such as magnetic resonance imaging (MRI) images typically requires a clinician to synthesize information across several imaging sequences (e.g., T1-weighted, T2-weighted, FLAIR, diffusion-weighted imaging (DWI), apparent diffusion coefficient (ADC), post-contrast T1, etc.) and across different views (e.g., axial/transverse, sagittal, coronal, etc.). As part of the efforts to automate this process, attempts have been made in recent years to use artificial intelligence (AI) technologies to learn the correlation between certain medical images and a corresponding medical report, with the hope to gain insight into what features in the medical images may have led to a particular clinical diagnosis or medical decision. Some of the technologies that have been attempted rely on registering images from different sequences or views at the pixel level, and then aligning the registered images with texts from a medical report. In routine clinical practice, however, the set and quality of medical image sequences may vary by patient, scanner, and site protocol. For example, a DWI image may exhibit geometric distortion, and thick axial slices may obscure findings that would be more apparent in sagittal views. This heterogeneity, along with frequently missing sequences, makes registration-based approaches unreliable, computationally burdensome, and susceptible to artifacts that can degrade subsequent tasks.

Other attempted approaches employ static neural network architectures and often require a fixed number and ordering of image sequences as inputs and a separate processing module for each input sequence, leading to excessive parameters, poor extensibility, and reduced robustness (e.g., when one or more sequences are missing).

Correlating complex medical reports with specific image features presents additional challenges. This is because clinical medical reports typically describe a medical examination as a whole, with interleaving statements related to findings from multiple sequences and/or views. On the other hand, methods that require splitting a medical report into sentence-level or sequence-level captioning of each individual image demand significant manual efforts and can fracture the clinical context that often guides real-world decision-making.

Accordingly, there is a need to develop techniques that can (i) accept dynamic multi-sequence, multi-view inputs with variable counts, (ii) avoid reliance on pixel-level image registration, and (iii) accurately align image features with specific diagnoses a comprehensive medical report.

SUMMARY

Described herein are systems, methods, and apparatus for aligning medical images (MRI images) with medical reports based on dynamic multi-sequence, multi-view inputs. According to embodiments of the present disclosure, an apparatus may obtain a plurality of MRI images of a patient and a medical report for the patient, wherein the plurality of MRI images may be associated with respective sequence labels and respective view labels, and wherein the medical report may include multiple diagnoses. The apparatus may determine respective image-type embeddings for the plurality of MRI images (e.g., using a look-up table) based on the respective sequence labels and the respective view labels associated with the plurality of MRI images. The apparatus may further encode, using a universal image encoder, respective features of the plurality of MRI images into respective image-content embeddings, wherein the universal image encoder may be configured to encode two or more types of MRI images using a same set of parameters. The apparatus may fuse the respective image-type embeddings and the respective image-content embeddings associated with the plurality of MRI images into a first image feature representation for the plurality of MRI images.

The apparatus may further encode, using a text encoder, textual features of the medical report into a text feature representation. The apparatus may then calculate a first similarity score based on the first image feature representation derived for the plurality of MRI image and the text feature representation derived for the medical report, wherein the first similarity score may indicate a match between the first image feature representation and the text feature representation. Additionally, the apparatus may fuse the respective image-type embeddings and the respective image-content embeddings for a subset of the plurality of MRI images into a second image feature representation, wherein the subset of MRI images may include at least one fewer MRI image than the plurality of MRI images. The apparatus may calculate a second similarity score based on the second image feature representation derived for the subset of MRI images and the text feature representation derived for the medical report, wherein the second similarity score may indicate a match between the second image feature representation and the text feature representation. The apparatus may then determine a contribution of the at least one MRI image missing from the subset of MRI images to the multiple diagnoses based on a difference between the first similarity score and the second similarity score, and provide an indication of the determined contribution.

The universal image encoder may be trained using multiple sets of training MRI images and multiple training medical reports in a training batch, wherein each medical report may be associated with a corresponding set of training MRI images. During the training of the universal image encoder, respective hash values may be calculated for the multiple training medical reports included in the training batch, and the hash values may be used to eliminate or prevent duplicity in the multiple training medical reports of the training batch. In addition, a similarity between each set of training MRI images and a corresponding training medical report may be determined in a shared feature space based on an average of a first similarity score and a second similarity score calculated for the set of training MRI images and the corresponding training medical report.

In examples, the apparatus may sum or average the image-type embedding and the image-content embedding of each of the plurality of MRI images into a combined image embedding for each MRI image. The apparatus may then aggregate the combined image embedding determined for each of the plurality of MRI images into the first feature representation via average pooling.

In examples, the plurality of MRI images may include a first MRI image and a second MRI image, wherein the first MRI image may have a sequence label indicating that the first MRI image is a T1 image and the second MRI image may have a sequence label indicating that the second MRI image is a T2 image. In addition, the first MRI image may have a view label indicating that the first MRI image includes an axial view and the second MRI image may have a view label indicating that the second MRI image includes sagittal view.

In examples, the medical report described herein may include respective textual descriptions for the plurality of MRI images, and wherein the multiple diagnoses in the medical report may be made based on two or more of the plurality of MRI images.

In examples, the apparatus may calculate the first similarity score based on a cosine similarity between the first image feature representation and the text feature representation, and calculate the second similarity score based on a cosine similarity between the second image feature representation and the text feature representation.

In examples, the apparatus may indicate the contributions of the plurality of MRI images to the multiple diagnoses as a visualization of ranked contribution scores together with the respective sequence and view labels of the plurality of MRI images.

In examples, the universal image encoder may be trained using a contrastive learning technique to match the first image feature representation and the text feature representation (e.g., with respect to an anatomical abnormality of the patient).

In examples, the text encoder may include a bidirectional text encoder implemented using a transformer architecture.

BRIEF DESCRIPTION OF THE DRAWINGS

A more detailed understanding of the examples disclosed herein may be had from the following description, given by way of example in conjunction with the accompanying drawing.

FIG. 4 is a flow diagram illustrating an example process for correlating MRI images with a medical report and quantifying the contribution of particular images to the diagnoses in the medical report.

DETAILED DESCRIPTION

The present disclosure is illustrated by way of example, and not by way of limitation, in the figures of the accompanying drawings. A detailed description of illustrative examples will be provided with reference to the figures. Although these examples may be described with certain technical details, it should be noted that the details are not intended to limit the scope of the disclosure. Further, while some examples may be described in a medical setting, those skilled in the art will understand that the techniques disclosed in those examples may be applicable to other settings or use cases as well.

Figure 1:
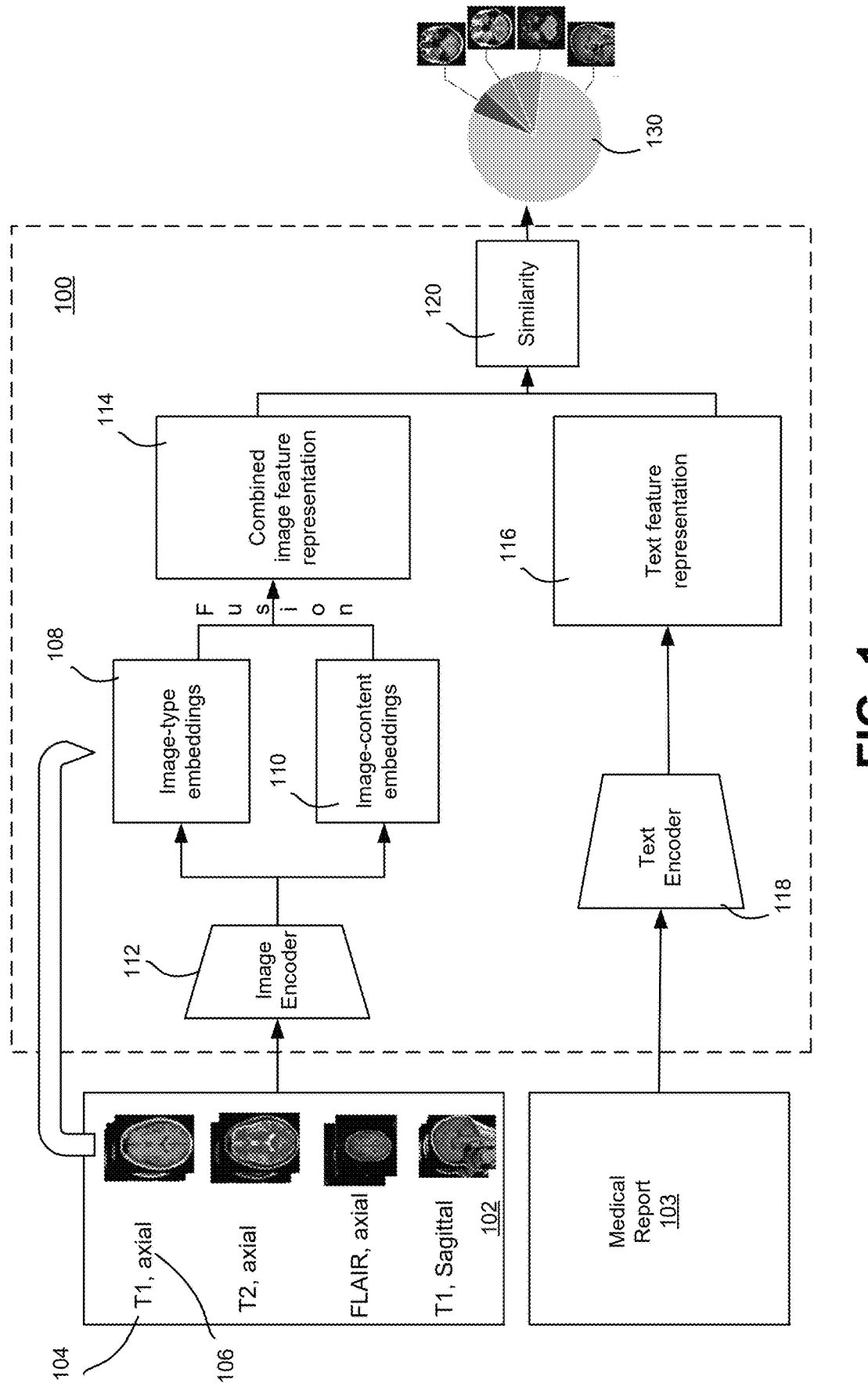
FIG. 1 is a simplified block diagram illustrating an example of correlating MRI images with a medical report and quantifying the contribution of particular MRI images to the diagnoses in the medical report.

FIG. 1 illustrates an example of an apparatus 100 configured to correlate medical imaging results (e.g., MRI imaging results) of a patient with medical reports for the patient and quantify the contribution of particular MRI images to specific diagnoses in the medical reports. As shown in FIG. 1, the apparatus 100 may receive multiple medical images 102 of the patient and a medical report 103 for the patient. The medical images 102 (e.g., MRI images) may be associated with respective sequence labels 104 and respective view labels 106. The sequence labels 104 may identify the respective sequence types or contrasts of the medical images such as, e.g., T1, T2, FLAIR, DWI, ADC, post-contrast T1, etc., and the view labels 106 may specify the respective views or imaging planes of the medical images such as, e.g., axial/transverse, sagittal, coronal, etc. In examples, the sequence labels 104 and view labels 106 may be extracted from the metadata associated with the medical images 102 (e.g., via the SeriesDescription, SequenceName, andImageOrientationPatient properties of Digital Imaging and Communications in Medicine (DICOM) metadata).

The medical report 103 may include text-based image descriptions, observations, and/or diagnostic conclusions associated with multiple image sequences. For example, the image descriptions and observations may recite "focal DWI hyperintensity with ADC hypointensity in the right MCA territory, patchy periventricular/deep white-matter FLAIR hyperintensities, or a right basal ganglia hematoma with surrounding edema," and the diagnostic conclusions may include "acute infarct in the right MCA territory, chronic microangiopathic change, and acute intraparenchymal hemorrhage of the right basal ganglia." In some cases, the medical report may refer to anatomical structures and abnormalities (e.g., infarct, mass effect, demyelination, etc.) and draw on information from different image sequences and views without naming each image. The medical report 103 may be a full, original report comprising information about multiple image sequences rather than a report that has already been separated (e.g., manually) into per-sequence or per-image segments.

For each medical image 102, the apparatus 100 may obtain a respective image-type embedding 108. The apparatus 100 may do so, for example, using a lookup table that maps each image's sequence and view labels to an image-type embedding. As such, the apparatus 100 may use the sequence and view labels as a composite key to find the corresponding embedding (e.g., (sequence=T1, view=sagittal)→$e_{type}$). In some implementations, separate learnable tables may be maintained for sequences and views, and the apparatus 100 may retrieve e_seq[T1] from a sequence look-up table, retrieve e_view[sagittal] from a view look-up table, then combine them via summation or concatenation followed by a linear projection to produce a fixed-dimension image-type embedding (e.g., a 64-D or 128-D embedding). All embedding entries may be learnable parameters updated during training so that the mapping may evolve to support downstream image-text alignment.

The apparatus 100 may additionally extract image features from each medical image 102 and encode those features into a respective image-content embedding 110. Instead of using a separate image encoder for each type of image sequence or view, the apparatus 100 may employ a universal image encoder 112 that is capable of processing images of different sequences and/or views using a same set of parameters. Greater details about the universal image encoder 112 will be provided further below.

The apparatus 100 may fuse the respective image-type embeddings 108 and the respective image-content embeddings 110 for the multiple images 102 into a combined image feature representation 114 (e.g., a feature vector or feature map) representative of the multiple images 102 as a whole. In examples, the fusion may be accomplished by projecting the respective image-type embedding 108 and the respective image-content embedding 110 for each input image 102 to a common dimensionality and then combining the embeddings (e.g., via summation, averaging, concatenation, or a learned gated fusion function) to form a per-image feature representation (e.g., a feature vector). The apparatus 100 may then aggregate the per-image feature representation across all input images (e.g., via average pooling, which may be order-invariant and capable of accommodating a variable number of inputs) to yield the combined image feature representation 114. In some implementations, the aggregation may be weighted (e.g., by estimated image quality or confidence), and one or more pooled vectors may be normalized and/or passed through a projection head to align with a shared image-text space.

The apparatus 100 may extract text features from the medical report 103 and encode those features into a text feature representation 116 (e.g., a feature vector or feature map) using a text encoder 118. For example, report texts may be normalized (e.g., via lowercasing and punctuation/whitespace cleanup), tokenized, and passed through the text encoder 118 to produce per-token hidden states from which a report-level embedding may be derived (e.g., via CLS pooling or mean pooling). The report-level embedding may then be mapped, via a projection head (e.g., a linear layer), to a shared image-text space and normalized (e.g., L2-normalized) to yield the text feature representation 116.

In some examples, the universal image encoder 112 may be a 3D vision transformer (ViT), and the text encoder 118 may be a bidirectional text encoder implemented based on a transformer architecture. As mentioned earlier, the universal image encoder 112 may be capable of encoding two or more types of medical images (e.g., MRI images of different sequences and/or views) using the same set of parameters. For example, the universal image encoder 112 may include a single, parameter-sharing backbone (e.g., a 3D ViT or a 3D ResNet) configured to process T1, T2, FLAIR, DWI, ADC, and post-contrast T1 images, as well as images having axial, sagittal, or coronal views. Compared to using different encoders for difference image types, the use of a universal encoder may reduce model size, simplify deployment, improve generalization to variable input sets (including missing sequences), and allow for order- and count-agnostic aggregation.

The image encoder 112 may be implemented using a vision transformer. In some implementations, such a vision transformer may include multiple components, such as, e.g., a feature extractor and a transformer encoder. The feature extractor may include a convolutional neural network (CNN) configured to extract features (e.g., local features) from an input image. The extracted features may be then flattened into a feature representation (e.g., such as a two-dimensional (2D) feature vector) and fed into the transformer encoder. The transformer encoder may include multiple layers, each of which may include a multi-head self-attention layer and/or a feedforward layer. The self-attention layer may allow the transformer to attend to different parts of the feature sequence and learn relationships between them, while the feedforward layer may apply a non-linear transformation to each feature vector. Residual connections and layer normalization may be applied after a sub-layer, for example, to stabilize the training of the transformer neural network. Using such an architecture, an entire image may be processed at once, for example, without spatial pooling. In some implementations, the output of the transformer neural network may include a sequence of feature vectors, each of which may correspond to a different patch in the input image.

The text encoder 118 may also be implemented using a transformer architecture. In some implementations, such a transformer may include an encoder and/or a decoder, each of which may include multiple layers. The encoder may be configured to receive a sequence of input tokens (e.g., the words in a textual description) and generate a sequence of hidden representations or embeddings that may capture the meaning of each token. An encoder layer may include multiple (e.g., two) sub-layers, such as, e.g., a multi-head self-attention layer and a position-wise feedforward layer. The self-attention layer may allow the transformer network to attend to different parts of the input sequence and learn the relationships between them. For example, via the self-attention layer, a weighted sum of the input tokens may be calculated, where the relevant weights may be determined through a learned attention function that accounts for the similarity between each token and all other tokens in the sequence. The feedforward layer may then apply a non-linear transformation to each token's hidden representation, allowing the neural network to capture complex patterns in the input sequence. Residual connections and/or layer normalization may be used and/or applied after each sub-layer to stabilize the training of the network. The decoder of the transformer architecture may be configured to receive a sequence of target tokens and generate a sequence of hidden representations (e.g., embeddings) that may capture the meaning of each target token, conditioned on the encoder's output. A decoder layer may include multiple (e.g., two) sub-layers, such as, e.g., a masked multi-head self-attention layer, which may attend to target tokens that have already been generated, and a multi-head attention layer, which may attend to the encoder's output. The masked self-attention layer may allow the neural network to generate the target tokens one at a time, while preventing it from looking ahead in the sequence. The multi-head attention layer may attend to the encoder's output to help the neural network generate target tokens that may be semantically related to the input sequence. The decoder may also include a position-wise feedforward layer and may use or apply residual connections and/or layer normalization after each sub-layer (e.g., similar to the encoder).

The apparatus 100 may correlate (e.g., align) certain features of the input images 102 with specific diagnoses in the medical report 103 by determining a similarity 120 between the combined image feature representation 114 and the text feature representation 116. The apparatus 100 may further determine the contribution of each specific image 102 to the diagnoses utilizing the similarity 120. For example, the apparatus 100 may compute a first similarity score by comparing the combined image feature representation 114 (e.g., a first combined image feature representation) with the text feature representation 116 in a shared image-text feature space. This first similarity score may reflect how well the aggregated image features of all of the input images 102 match the diagnostic content of the medical report 103 (e.g., a higher score may indicate a stronger match or correlation between the image features and the medical report with respect to a reported anatomical abnormality). Then, to attribute the diagnoses in the medical report 103 to the contribution of each input image 102, the apparatus 100 may obtain a subset of the input images 102, for example, by excluding at least one input image from the subset, recompute a combined image feature representation (e.g., a second combined image feature representation) based on the subset of images (e.g., using the same fusion techniques), and calculate a second similarity score between the second combined image feature representation (e.g., representative of the subset of images) and the text feature representation 116. The contribution of the image i missing from the subset of images may then be determined as a difference $C_i = S_{all} - S_{-i}$, where $S_{all}$ is the first similarity score computed using all of the input images 102, and $S_{-i}$ is the second similarity score computed using the subset of images that does not image i. A greater difference may indicate a greater contribution of the excluded MRI image to the diagnostic content of the medical report 103 (including its multiple diagnoses), whereas a smaller difference may indicate a smaller contribution. A difference value equal to or near zero may indicate that the excluded image is largely redundant or non-informative. This procedure may be repeated for each image present at the input and the contributions of multiple images (e.g., all of the images 102) may be normalized (e.g., $C_i/S_{all}$) and/or ranked to generate an indication of their diagnostic importance and an explanation of how a certain diagnosis may have been derived.

The apparatus 100 may provide an indication 130 of the determined contribution of each image 102. For example, the apparatus 100 may render a visualization of the per-image (and/or per-sequence) contribution scores together with the sequence and/or view labels of the images on a display device. The apparatus 100 may rank the contributions, for example, from highest to lowest in the visualization. In examples, the visualization may be provided as a bar chart or a table with color-coding proportional to the scores. Selecting an entry (e.g., "T1-sagittal: 0.14") in the chart or table may cause the corresponding image to be highlighted and relevant texts from the medical report (e.g., the sentence referencing an anatomical abnormality) to be displayed. In some examples, the indication further includes a top-k list, a threshold flag (e.g., "flag any contribution score ≥0.10"), and/or an exportable record (e.g., a JSON or report note) summarizing the ranked contributions for audit and clinical review.

It should be noted that although FIG. 1 illustrates an example of using similarity scores to determine the contribution of a medical image to a diagnosis, the techniques may also be used to train the universal image encoder 112 such that it may become capable of identifying the image features (e.g., encoded in a feature embedding) from multiple types of medical images that are most relevant to an anatomical structure or a medical abnormality. The image encoder 112 may then be used for a variety of downstream tasks, including, for example, automatic medical report generation based on a given set of medical images.

Figure 2:
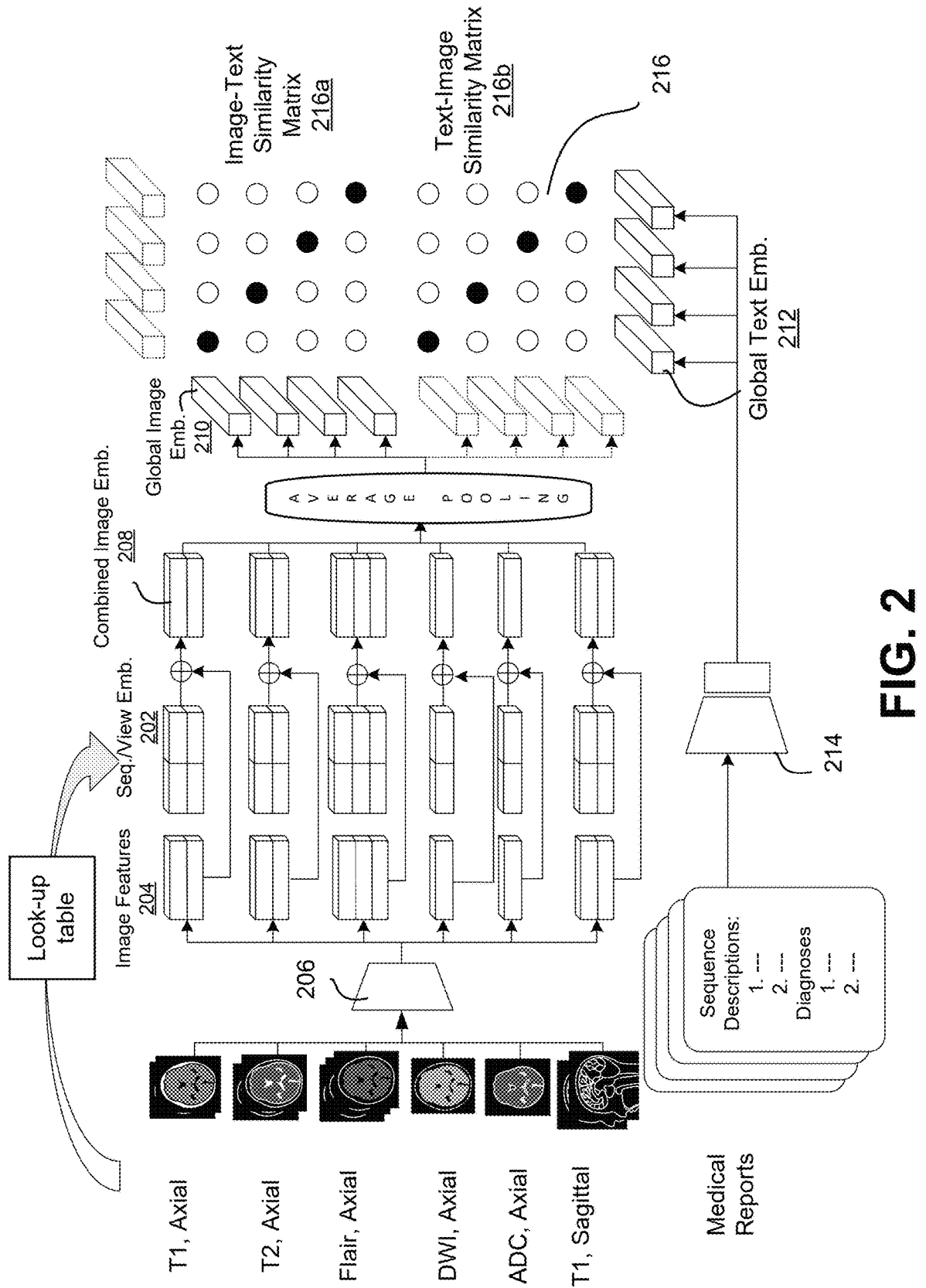
FIG. 2 is a simplified block diagram illustrating an example of training a machine learning (ML) based system to fuse different image embeddings into a global image feature representation for a plurality of MRI images and correlate the global image feature representation with a text feature representation derived from a medical report.

FIG. 2 illustrates an example of training an ML-based system (e.g., the apparatus 100 of FIG. 1) to derive and fuse image-type embeddings and image-content embeddings associated with a plurality of MRI images into a global image feature representation (e.g., the combined image feature representation 114 of FIG. 1) for the plurality of MRI images, and correlate the global image feature representation with a text feature representation (e.g., the text feature representation 116 of FIG. 1). Four sets of multi-sequence, multi-view MRI images and four clinical medical reports are used in this example as image-text pairs for training the ML models involved. Three of the four sets of images contain a FLAIR axial image, two of the four sets contain a T1 axial image, a T2 axial image, and a T1 sagittal image, and one of the four sets contains a DWI axial image and an ADC axial image. As such, image set A may include a T1 axial, a T2 axial, a FLAIR axial, a DWI axial, and an ADC axial, image set B may include a T1 axial, a T2 axial, and a T1 sagittal, image set C may include a FLAIR axial and a T1 sagittal, and image set D may include a FLAIR axial. Each set of images may correspond to a medical report (e.g., report A, report B, report C, or report D).

As shown in FIG. 2, an image-type embedding 202 may be derived for an input MRI image (e.g., from any of the four image sets) based on a sequence label (e.g., indicating a sequence type of T1, T2, FLAIR, DWI, ADC, or post-contrast T1) and a view label (e.g., indicating an axial/transverse view, a sagittal view, or a coronal view) associated with the image, and by looking up the embedding from a lookup table (e.g., the look-up table may include a predetermined label-to-embedding mapping). For each input MRI image, an image-content embedding 204 may also be derived using a universal image encoder 206 (e.g., the image encoder 112 of FIG. 1), and the image-content embedding 204 and the image-type embedding 202 for that MRI image may be combined to form a per-image combined feature embedding 208. The combination (e.g., fusion) may be accomplished using various suitable techniques including, for example, via a summation of the embeddings (e.g., after projecting the embeddings to a common size), a concatenation of the embeddings, or a gated fusion (e.g., using a learned gating function). The resulting per-image combined feature embedding 208 may capture not only what the corresponding MRI image depicts (e.g., reflecting the content of the image), but also what type of MRI image it is (e.g., reflecting the sequence/view identity of the image). The feature embeddings for all of the MRI images in an image set may be further fused (e.g., combined) into a global feature representation 210 for the image set, for instance, via average pooling. Using the four training image sets shown in FIG. 2 as an example, four global feature representations $v_A, v_B, v_C, v_D \in \mathbb{R}^d$ may be derived for the four image sets by average-pooling the combined feature embedding 208 of each training image in each training image set as follows: $v_A$=AveragePooling($e_{T1}$, $e_{T2}$, $e_{FLAIR}$, $e_{DWI}$ $e_{ADC}$), $v_B$=AveragePooling($e_{T1}$, $e_{T2}$, $e_{T1\_SAG}$), $v_C$=AveragePooling ($e_{FLAIR}$, $e_{T1\_SAG}$), and $v_D$=AveragePooling($e_{FLAIR}$). The pooling may be performed in an order-invariant manner and may support a variable number of inputs, making the representation robust to missing sequences/views. In some examples, the pooling may be weighted (e.g., by image quality or confidence scores), and the resulting global image embedding 210 (e.g. a feature vector or a feature map) may be projected and/or normalized (e.g., L2-normalized) to match other embeddings in a shared image-text feature space. It should be noted the aforementioned techniques do not limit the size of the training batch to 4, and may be used for other batch sizes including, for example, a training batch that contains 8, 16, 32, etc. sets of images and corresponding reports.

As shown in FIG. 2, parallel to the derivation of global image representations 210, a global text representation 212 may be derived from each input medical report (e.g., one of the four medical reports in the training batch) using a text encoder 214 (e.g., the text encoder 118 of FIG. 1). The global image representation 210 associated with each input image set and the global text representation 212 associated with each input medical report may then be projected into a shared feature space 216 to calculate a similarity score between the global image representation for each image set and the global text representation for each medical report. The similarity score may be calculated using various suitable techniques including, for example, a cosine similarity between the global image representation and the global text representation (e.g., which may be two feature vectors). As illustrated in FIG. 2, the similarity scores calculated for a single global image representation across the four global text representations (e.g., referred to herein as along an image axis) may form a 4×4 image-text similarity matrix 216a. Symmetrically, the similarity scores calculated for a single global text representation across the four global image representations (e.g., referred to herein as along a text axis) may form a 4×4 text-image similarity matrix 216b. An overall similarity score between each global image representation and each global text representation may be calculated as the average of the corresponding similarity scores in the two matrices, and the parameters of the image encoder 206 and/or the text encoder 214 may be optimized with a goal to maximize the scores at the diagonal positions (e.g., this has the effect of pulling matched image set and medical report together and pushing unmatched image set and medical report farther apart).

In examples, when conducting the training illustrated in FIG. 2, data in the same training batch may be preprocessed to eliminate duplicity in the data. For example, to avoid label ambiguity that may otherwise arise in contrastive learning if duplicated medical reports are used in the training batch, a content signature (e.g., a hash value such as an MD, certain keywords, etc.) may be computed for each medical report in the batch, and a uniqueness constraint may be enforced within the batch based on the content signature for each report. That is, a report having the same or substantially similar content signature as another report of the same batch may be excluded from the training batch. By maintaining the uniqueness of the reports used in the batch, sample quality may be improved, symmetric image-to-text/text-to-image losses may be stabilized, and training convergence may be accelerated. In some examples, before the hash value is calculated for a report, the report content may be normalized, for example, via lowercasing, whitespace/punctuation normalization, and/or headers removal.

Figure 3:
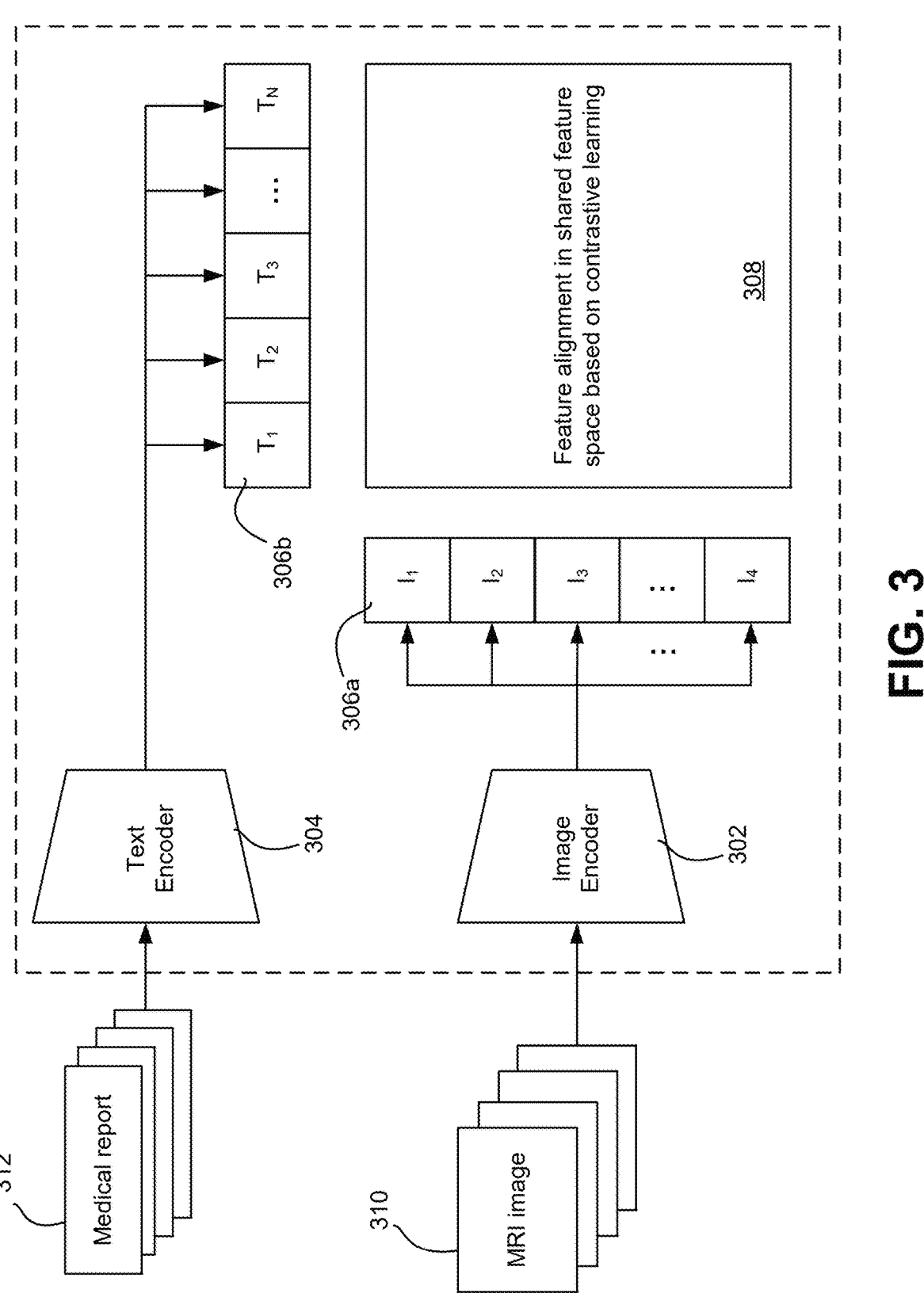
FIG. 3 is a simplified block diagram illustrating an example of training an ML model for extracting features from paired images and textual descriptions and learning the correlation between the images and text descriptions.

FIG. 3 illustrates an example of training an image encoder 302 and a text encoder 304 (e.g., the image encoder 112 and the text encoder 118 of FIG. 1) to extract features from MRI images and medical reports, respectively, and match the extracted image features 306a and text features 306b in a shared embedding space 308. The training of the image encoder 302 may be conducted using a large dataset that may include MRI images 310. The training of the text encoder 304 may be conducted using a large dataset that may include medical reports 312. The training data for the image encoder 302 and the text encoder 304 may be obtained from various sources including, for example, the Internet (e.g., medical websites that may include medical images and corresponding textual descriptions that describe the content of the images), publicly accessible databases (e.g., figures and captions from repositories of academia publications), hospital records or medical reports (e.g., radiology reports), etc. The training data may be pre-processed, for example, to ensure that it is in a suitable format for the training. The pre-processing may involve resizing the images, tokenizing the text, creating pairs of image-text inputs, etc. The pre-processing may also include augmenting the training data (e.g., by adding textual descriptions comprising negative terms to the training dataset) to improve the robustness and accuracy of the image encoder 302 and the text encoder 304.

As shown in FIG. 3, the image encoder 302 may be implemented as a vision-transformer architecture configured to extract image features 306a from input images 310, and the text encoder 304 may be implemented as a bidirectional text transformer configured to extract text features 306b from medical reports 312. In some examples, the image encoder 302 and the text encoder 304 may be first pretrained (e.g., separately) on large image and text corpora and then trained together end-to-end with a contrastive objective to pull matched image-text pairs close together and push mismatched pairs further apart in the shared feature space 308. Contrastive losses such as normalized temperature-scaled cross-entropy (NT-Xent/InfoNCE) may be used to optimize the parameters of the encoders (and any projection heads into the shared space). The encoders may subsequently be fine-tuned on an application-specific dataset (e.g., clinical MRI images and associated medical reports) and/or for various downstream tasks. At an inference time, given a report and one or more MRI images, the image and text encoders may predict and project image/text embeddings into the shared representation space 308, based on which a matching or similarity score may be calculated (e.g., based on the cosine similarity of the embeddings) to indicate how well the embeddings match each other.

In examples, the shared feature space 308 may include an image axis and a text axis. For a given training iteration, a similarity matrix may be formed between the image features 306a (e.g., image embeddings) and the text features 306b (e.g., text embeddings). The similarity of a particular image-text pair may be computed using a cosine similarity between the image and text features, such that each element in the matrix may reflect how well an image embedding matches a text embedding within the shared space. An image-axis loss (image→text) may then be computed by treating each image embedding as a query over all text embeddings in the iteration. Symmetrically, a text-axis loss (text→image) may be computed by treating each text embedding as a query over all image embeddings in the iteration. The training loss may be determined as an average of the image-axis loss and the text-axis loss, thereby enforcing symmetric alignment that may increase the similarity for matched image-text pairs and decrease the similarity for mismatched image-text pairs.

FIG. 4 illustrates an example process 400 for correlating (e.g., aligning) medical images (e.g., MRI images) with a medical report and quantifying the contribution of particular images to the diagnoses in the medical report. As shown in FIG. 4, the process 400 may include obtaining a plurality of medical images of a patient and a medical report for the patient at 402, wherein the plurality of medical images may be associated with respective sequence labels and respective view labels, and wherein the medical report may include multiple diagnoses. The process 400 may further include determining, using a look-up table, respective image-type embeddings for the plurality of medical images based on their sequence labels and view labels. At 406, the process 400 may include encoding, using a universal image encoder, features of the plurality of medical images into respective image-content embeddings, wherein the universal image encoder may be configured to encode two or more types of medical images using a same set of parameters. At 408, the process 400 may include fusing the respective image-type embeddings and the respective image-content embeddings of the medical images into a first image feature representation. At 410, the process 400 may include encoding, using a text encoder, features of the medical report into a text feature representation. At 412, the process 400 may include calculating a first similarity score based on the first image feature representation and the text feature representation, wherein the first similarity score may indicate a match between the first image feature representation and the text feature representation with respect to an anatomical abnormality of the patient. At 414, the process 400 may further include fusing the respective image-type embeddings and the respective image-content embeddings of a subset of the plurality of medical images into a second image feature representation, wherein the subset of medical images may include at least one fewer image than the plurality of medical images. At 416, the process 400 may include calculating a second similarity score based on the second image feature representation and the text feature representation, wherein the second similarity score may indicate a match between the second image feature representation and the text feature representation (e.g., with respect to an anatomical abnormality of the patient). At 418, the process 400 may include determining a contribution of the at least one medical image missing from the subset of medical images to the multiple diagnoses based on a difference between the first similarity score and the second similarity score. At 420, the process 400 may further include providing an indication of the determined contribution.

In examples, the universal image encoder described above may be trained using multiple sets of training MRI images and multiple training medical reports, wherein each medical report may be associated with a corresponding set of training MRI images. During the training of the universal image encoder, respective hash values may be calculated for the multiple training medical reports and used to eliminate or prevent duplicity in the multiple training medical reports. In addition, a similarity between each set of training MRI images and a corresponding training medical report may be determined in a shared feature space based on an average of a first similarity score and a second similarity score calculated for the set of training MRI images and the corresponding training medical report.

In examples, the fusion described above may be accomplished by summing or averaging the image-type embedding and the image-content embedding of each of the plurality of medical images into a combined image embedding for the medical image. The combined image embeddings determined for all of the medical images may then be aggregated into the first feature representation, for example, via average pooling.

In examples, the plurality of medical images described above may include a first MRI image and a second MRI image, wherein the first MRI image may have a sequence label indicating that the first MRI image is a T1 image and the second MRI image may have a sequence label indicating that the second MRI image is a T2 image. In addition, the first MRI image may have a view label indicating that the first MRI image includes an axial view and the second MRI image may have a view label indicating that the second MRI image includes sagittal view.

In examples, the medical report described above may include respective textual descriptions for the plurality of MRI images, and the multiple diagnoses in the medical report may be made based on two or more of the plurality of MRI images.

In examples, the first similarity score described above may be calculated based on a cosine similarity between the first image feature representation and the text feature representation, and the second similarity score described above may be calculated based on a cosine similarity between the second image feature representation and the text feature representation.

In examples, the respective contributions of the plurality of medical images to the multiple diagnoses in the medical report may be indicated as a visualization of ranked contribution scores together with the respective sequence and view labels of the plurality of medical images.

In examples, the universal image encoder described above may be trained using a contrastive learning technique to match the first image feature representation and the text feature representation with respect to the anatomical abnormality of the patient.

In examples, the text encoder described above may include a bidirectional text encoder implemented using a transformer architecture.

Figure 5:
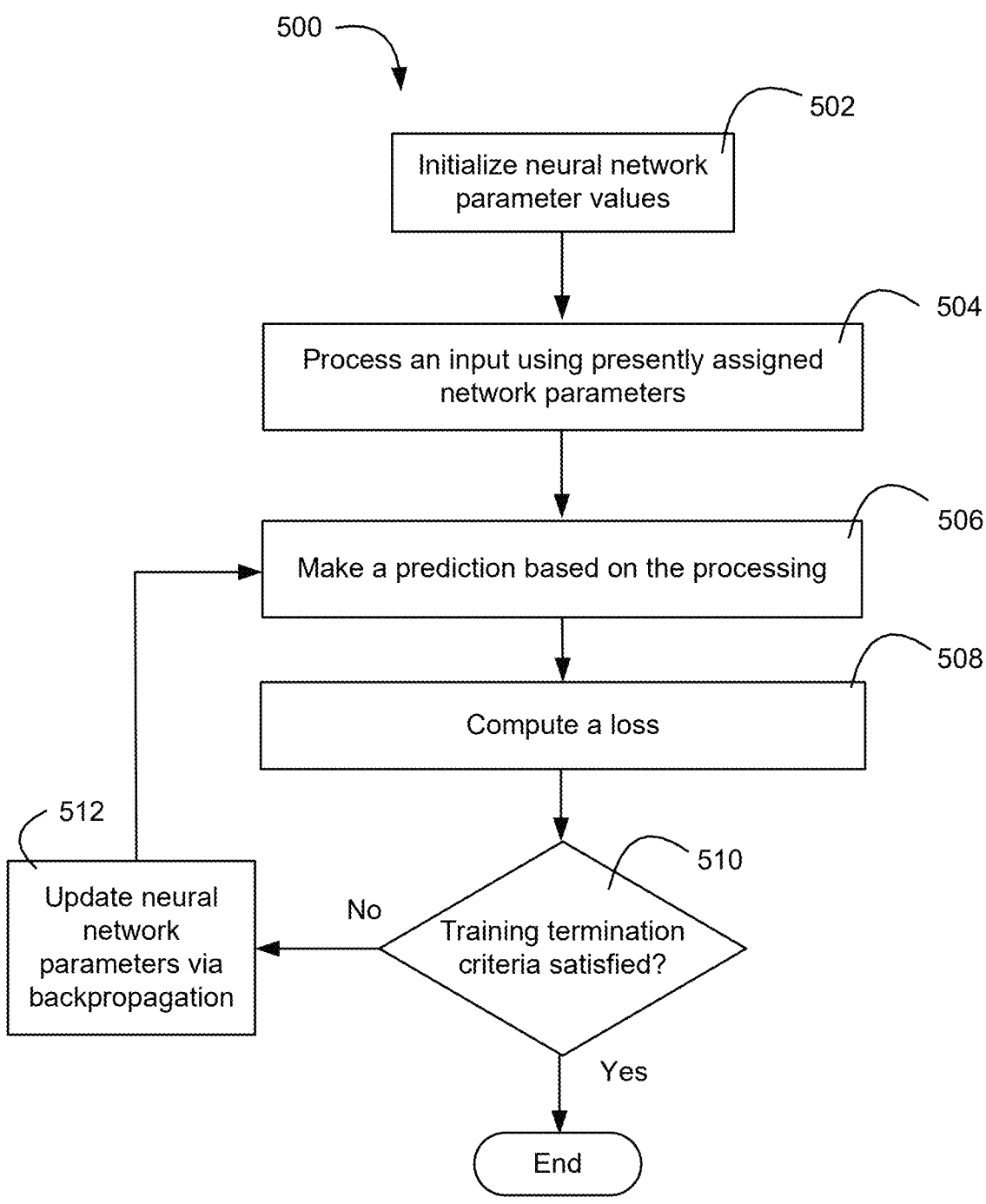
FIG. 5 is a flow diagram illustrating example operations that may be associated with training an artificial neural network to learn one or more of the ML model described herein.

FIG. 5 illustrates example operations 500 that may be associated with training an artificial neural network to learn the encoders described herein. As shown in FIG. 5, the training operations 500 may include initializing the operating parameters of the neural network (e.g., weights associated with various layers of the neural network) at 502, for example, by sampling from a probability distribution or by copying the parameters of another neural network having a similar structure. The training operations 500 may further include processing an input at 504 using presently assigned parameters of the neural network and making a prediction at 506 based on the processing. The training operations 500 may further include calculating a loss associated with the prediction at 508, and determining, at 510, whether one or more training termination criteria are satisfied based on the loss. For example, the training termination criteria may be determined to be satisfied if the loss is smaller than a threshold. If the determination at 510 is that the termination criteria are satisfied, the training may end; otherwise, the presently assigned network parameters may be adjusted at 512, for example, by backpropagating a gradient descent of the calculated loss through the neural network, before the training returns to 506.

For simplicity of explanation, the training operations 500 are depicted and described with a specific order. It should be appreciated, however, that the training operations 500 may occur in various orders, concurrently, and/or with other operations not presented or described herein. Furthermore, it should be noted that not all operations that may be included in the training method are depicted and described herein, and not all illustrated operations are required to be performed. Further, the neural network described herein may include an image encoder pretrained for image-only tasks and/or a text encoder pretrained for text-only tasks. In those situations, the weights of one of the image encoder or the text encoder may be partially frozen during the training of the other encoder (e.g., not updated during the training process).

Figure 6:
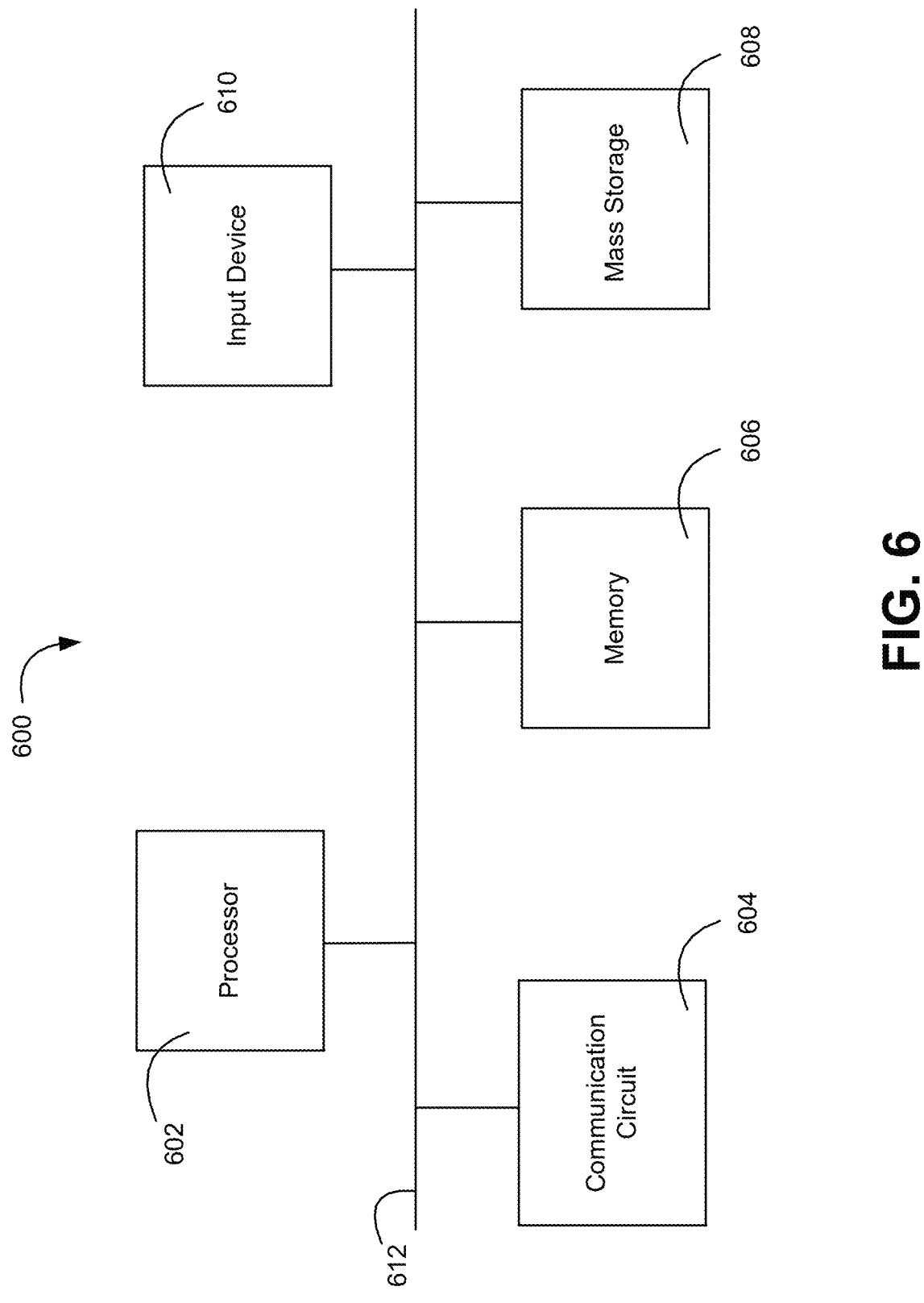
FIG. 6 is a block diagram illustrating example components of an apparatus that may be configured to perform the tasks described herein.

The systems, methods, and/or instrumentalities described herein may be implemented using one or more processors, one or more storage devices, and/or other suitable accessory devices such as display devices, communication devices, input/output devices, etc. FIG. 6 illustrates an example apparatus 600 that may be configured to perform the automatic image annotation tasks described herein. As shown, the apparatus 600 may include a processor (e.g., one or more processors) 602, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The apparatus 600 may further include a communication circuit 604, a memory 606, a mass storage device 608, an input device 610, and/or a communication link 612 (e.g., a communication bus) over which the one or more components shown in the figure may exchange information.

The communication circuit 604 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 606 may include a storage medium (e.g., a non-transitory storage medium) configured to store machine-readable instructions that, when executed, cause processor 602 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EE-PROM)), flash memory, and/or the like. The mass storage device 608 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 602. The input device 610 may include a keyboard, a mouse, a voice-controlled input device, a touch sensitive input device (e.g., a touch screen), and/or the like for receiving user inputs to the apparatus 600.

It should be noted that the apparatus 600 may operate as a standalone device or may be connected (e.g., networked, or clustered) with other computation devices to perform the functions described herein. And even though only one instance of each component is shown in FIG. 6, a skilled person in the art will understand that the apparatus 600 may include multiple instances of one or more of the components shown in the figure.

While this disclosure has been described in terms of certain examples and generally associated methods, alterations and permutations of the examples and methods will be apparent to those skilled in the art. Accordingly, the above description of example examples does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. An apparatus, comprising:
one or more processors configured to:
obtain a plurality of magnetic resonance imaging (MRI) images of a patient and a medical report for the patient, wherein the plurality of MRI images is associated with respective sequence labels and respective view labels, and wherein the medical report includes multiple diagnoses;
determine respective image-type embeddings for the plurality of MRI images based on the respective sequence labels and the respective view labels associated with the plurality of MRI images;
encode, using a universal image encoder, respective features of the plurality of MRI images into respective image-content embeddings, wherein the universal image encoder is configured to encode two or more types of MRI images using a same set of parameters;
fuse the respective image-type embeddings and the respective image-content embeddings of the plurality of MRI images into a first image feature representation for the plurality of MRI images;
encode, using a text encoder, textual features of the medical report into a text feature representation for the medical report;
calculate a first similarity score based on the first image feature representation for the plurality of MRI images and the text feature representation for the medical report;
fuse the respective image-type embeddings and the respective image-content embeddings for a subset of the plurality of MRI images into a second image feature representation, wherein the subset of MRI images includes at least one fewer MRI image than the plurality of MRI images;
calculate a second similarity score based on the second image feature representation for the subset of MRI images and the text feature representation for the medical report;
determine, based on a difference between the first similarity score and the second similarity score, a contribution of the at least one MRI image missing from the subset of MRI images to the multiple diagnoses included in the medical report; and
provide an indication of the determined contribution.

2. The apparatus of claim 1, wherein the one or more processors being configured to fuse the respective image-type embeddings and the respective image-content embeddings of the plurality of MRI images into the first image feature representation comprises the one or more processors being configured to sum or average the respective image-type embedding and the respective image-content embedding of each of the plurality of MRI images into a respective combined image embedding for the each of the plurality of MRI images.

3. The apparatus of claim 2, wherein the one or more processors being configured to fuse the respective image-type embeddings and the respective image-content embeddings of the plurality of MRI images into the first image feature representation further comprises the one or more processors being configured to aggregate the respective combined image embedding determined for the each of the plurality of MRI images into the first image feature representation via average pooling.

4. The apparatus of claim 1, wherein the plurality of MRI images comprises a first MRI image and a second MRI image, the sequence label of the first MRI image indicating that the first MRI image is a T1 image, the sequence label of the second MRI image indicating that the second MRI image is a T2 image.

5. The apparatus of claim 4, wherein the view label of the first MRI image indicates that the first MRI image includes an axial view, and wherein the view label of the second MRI image indicates that the second MRI image includes a sagittal view.

6. The apparatus of claim 1, wherein the medical report comprises respective textual descriptions for the plurality of MRI images, and wherein the multiple diagnoses in the medical report are made based on two or more of the plurality of MRI images.

7. The apparatus of claim 1, wherein the first similarity score is calculated based on a cosine similarity between the first image feature representation and the text feature representation, and wherein the second similarity score is calculated based on a cosine similarity between the second image feature representation and the text feature representation.

8. The apparatus of claim 1, wherein the indication comprises a visualization of the respective contributions determined for the plurality of MRI images together with the respective sequence labels and view labels of the plurality of MRI images.

9. The apparatus of claim 1, wherein the universal image encoder is trained using a contrastive learning technique to match the first image feature representation and the text feature representation with respect to an anatomical abnormality of the patient.

10. The apparatus of claim 1, wherein the text encoder is a bidirectional text encoder implemented using a transformer architecture.

11. The apparatus of claim 1, wherein the universal image encoder is trained using multiple sets of training MRI images and multiple training medical reports associated with a training batch, each of training medical report being associated with a corresponding set of training MRI images, and wherein, during the training of the universal image encoder:

respective hash values are calculated for the multiple training medical reports in the training batch and used to eliminate duplicate medical reports in the training batch; and a similarity between each set of training MRI images and a corresponding training medical report is determined in a shared feature space based on an average of a first similarity score and a second similarity score calculated for the set of training MRI images and the corresponding training medical report.

12. A method for sorting medical images, the method comprising:

obtaining a plurality of magnetic resonance imaging (MRI) images of a patient and a medical report for the patient, wherein the plurality of MRI images is associated with respective sequence labels and respective view labels, and wherein the medical report includes multiple diagnoses;

determining respective image-type embeddings for the plurality of MRI images using a look-up table and the respective sequence labels and the respective view labels associated with the plurality of MRI images;

encoding, using a universal image encoder, respective features of the plurality of MRI images into respective image-content embeddings, wherein the universal image encoder is configured to encode two or more types of MRI images using a same set of parameters;

fusing the respective image-type embeddings and the respective image-content embeddings into a first image feature representation for the plurality of MRI images;

encoding, using a text encoder, text features of the medical report into a text feature representation;

calculating a first similarity score based on the first image feature representation for the plurality of MRI images and the text feature representation for the medical report;

fusing the respective image-type embeddings and the respective image-content embeddings for a subset of the plurality of MRI images into a second image feature representation, wherein the subset of MRI images includes at least one fewer MRI image than the plurality of MRI images;

calculating a second similarity score based on the second image feature representation for the subset of MRI images and the text feature representation for the medical report;

determining a contribution of the at least one MRI image missing from the subset of MRI images to the multiple diagnoses based on a difference between the first similarity score and the second similarity score; and providing an indication of the determined contribution.

13. The method of claim 12, wherein fusing the respective image-type embeddings and the respective image-content embeddings into the first image feature representation comprises summing or averaging the respective image-type embedding and the respective image-content embedding of each of the plurality of MRI images to form a respective combined image embedding for the each of the plurality of MRI images.

14. The method of claim 13, wherein fusing the respective image-type embeddings and the respective image-content embeddings into the first image feature representation further comprises aggregate the respective combined image embedding determined for the each of the plurality of MRI images into the first image feature representation via average pooling.

15. The method of claim 12, wherein the plurality of MRI images comprises a first MRI image and a second MRI image, the sequence label of the first MRI image indicating that the first MRI image is a T1 image, the sequence label of the second MRI image indicating that the second MRI image is a T2 image.

16. The method of claim 15, wherein the view label of the first MRI image indicates that the first MRI image includes an axial view, and wherein the view label of the second MRI image indicates that the second MRI image includes a sagittal view.

17. The method of claim 12, wherein the first similarity score is calculated based on a cosine similarity between the first image feature representation and the text feature representation, and wherein the second similarity score is calculated based on a cosine similarity between the second image feature representation and the text feature representation.

18. The method of claim 12, wherein the indication comprises a visualization of the respective contributions determined for the plurality of MRI images together with the respective sequence labels and view labels of the plurality of MRI images.

19. The method of claim 12, wherein the universal image encoder is trained using a contrastive learning technique to match the first image feature representation and the text feature representation with respect to an anatomical abnormality of the patient, and wherein the text encoder is a bidirectional text encoder implemented based on a transformer architecture.

20. The method of claim 12, wherein the universal image encoder is trained using multiple sets of training MRI images and multiple training medical reports associated with a training batch, each of training medical report being associated with a corresponding set of training MRI images, and wherein, during the training of the universal image encoder:

respective hash values are calculated for the multiple training medical reports in the training batch and used to eliminate duplicate medical reports in the training batch; and a similarity between each set of training MRI images and a corresponding training medical report is determined in a shared feature space based on an average of a first similarity score and a second similarity score calculated for the set of training MRI images and the corresponding training medical report.

* * * * *